United States Patent
Rathod et al.

(10) Patent No.: US 6,872,936 B2
(45) Date of Patent: Mar. 29, 2005

(54) ACCELERATED WEATHERING APPARATUS

(75) Inventors: Rajen Rathod, Bartlett, IL (US); Richard D. Donato, Chicago, IL (US)

(73) Assignee: Atlas Material Testing Technology, L.L.C., Chicago, IL (US)

( * ) Notice: Subject to any disclaimer, the term of this patent is extended or adjusted under 35 U.S.C. 154(b) by 0 days.

(21) Appl. No.: 10/762,063

(22) Filed: Jan. 21, 2004

(65) Prior Publication Data

US 2004/0149922 A1 Aug. 5, 2004

Related U.S. Application Data

(62) Division of application No. 10/097,707, filed on Mar. 15, 2002, now Pat. No. 6,720,562.
(60) Provisional application No. 60/280,796, filed on Apr. 2, 2001.

(51) Int. Cl.[7] .......................... G01D 18/00; G01N 17/00
(52) U.S. Cl. ............................... 250/251.1; 250/492.1; 250/354.1; 250/395
(58) Field of Search ........................... 250/252.1, 492.1, 250/354.1

(56) References Cited

U.S. PATENT DOCUMENTS

| | | | | |
|---|---|---|---|---|
| 4,012,954 A | * | 3/1977 | Klippert | .................. 73/150 R |
| 4,544,995 A | | 10/1985 | Suga | |
| 5,206,518 A | * | 4/1993 | Fedor et al. | ............. 250/504 R |
| 5,220,840 A | * | 6/1993 | Neigoff et al. | ............. 73/865.6 |
| 5,414,325 A | * | 5/1995 | Allison | ..................... 315/158 |
| 6,285,137 B1 | * | 9/2001 | Grossman et al. | .......... 315/291 |
| 6,525,493 B2 | * | 2/2003 | Grossman et al. | .......... 315/291 |
| 6,720,562 B2 | * | 4/2004 | Rathod et al. | ............. 250/395 |

FOREIGN PATENT DOCUMENTS

| | | |
|---|---|---|
| DD | 207260 | 2/1984 |
| DE | 8906975 | 7/1989 |
| EP | 0487202 | 5/1992 |
| EP | 0550970 | 7/1993 |
| WO | WO0013001 | 3/2000 |

* cited by examiner

Primary Examiner—Albert Gagliardi
(74) Attorney, Agent, or Firm—Vedder Price Kaufman & Kammholz

(57) ABSTRACT

An apparatus for accelerated weathering testing specimens including discharge lamps as a concentrated light source for accelerating the deterioration of color, composition and/or structure of test specimens. Improved control calibration structures and methods of operation are also included. The test module to monitor the weathering test process from an improved location, detecting irradiance in the manner in which the specimens are exposed to such irradiance. The test modules are mounted in a pocket formed within the door for the test chamber such that the sensitive electronics of the modules are not exposed to the harsh environment within the test chamber, resulting in an exceptionally stable signal.

14 Claims, 15 Drawing Sheets

ACCELERATED WEATHERING APPARATUS

CROSS-REFERENCE TO RELATED APPLICATION

This application is a divisional of application Ser. No. 10/097,707, filed Mar. 15, 2002 U.S. Pat. No. 6,720,562 entitled "IMPROVED ACCELERATED WEATHERING APPARATUS", having as inventors, Rajen Rathod and Richard D. Donato.

This application claims the benefit of U.S. Provisional Application No. 60/280,796, filed Apr. 2, 2001.

FIELD OF THE INVENTION

This invention pertains to an apparatus for accelerating the weathering effects on test specimens, and more particularly, to an accelerated weathering apparatus having discharge lamps as a concentrated light source for accelerating the deterioration of color, composition, and/or structure of test specimens which includes improved control and calibration structure and methods of operation. The preferred embodiment of the present invention for testing specimens uses fluorescent ultraviolet lamps as the light sources that approximate natural sunlight in the ultraviolet portion of the spectrum and the deterioration caused thereby and will be described with particular reference thereto. However, it will be recognized that other discharge lamps may be used as sources, the primary example being xenon lamps or any other source.

BACKGROUND OF THE INVENTION

A conventional testing apparatus using discharge lamps as shown in FIG. 1 has eight ultraviolet lamps 10 provided in a test chamber 12 and arranged into symmetric downwardly divergent rows when viewed in cross-section. Specimens 14 to be tested are attached to two opposite specimen supporting walls of the housing of the test apparatus so as to face inwardly toward the lamps and receive the irradiance therefrom. In the machine shown, there are two specimens, an upper specimen and lower specimen; however, there may be only a single specimen or more than two. The rear surface of the specimens 14 is exposed to the atmospheric air outside the machine. Outside air is heated and blown into the interior of the chamber 12 to regulate the temperature in the chamber 12. Water in the moisture supply tank 16 is heated by conventional means and evaporated to supply moisture into the chamber 12.

In the above-described testing machine, one example of the machine's operation includes applying irradiance rays to the specimens 14 at a temperature of 60° C. for sixteen hours and then the lamps 10 are turned off and the interior of the chamber 12 is kept at 50° C. to create humidity for eight hours. These two steps, which constitute one cycle of a deterioration testing operation, are repeated continuously. While the lamps are off, the humidity in the chamber 12 is high, and the rear surface of the specimens is exposed to the outside air at a low temperature. Accordingly, the surfaces of the specimens are wetted due to condensation. Thus, the wetting of the specimens, the applying of ultraviolet irradiance, and the drying are repeated, which speeds the deterioration of the specimens. It is to be appreciated that the above description is just one type of cycle for which machines of this nature can be used.

Problems, however, exist with the apparatus shown in FIG. 1. Initially, there is no provision for sensing the output of the fluorescent lamps 10, in order to track their rate of degradation or control the irradiance output. A normal procedure for attempting to provide a uniform output from the lamps, in such a device, is to rotate the positions of the lamps at predetermined time intervals in a predetermined sequence. Testing of the lamps to detect actual output is not provided; rather, assumptions are made as to the likely output, and the rotation sequence is made in consideration of the assumptions.

Another drawback of this type of device is that there is no provision for conditioning the lamps during start-up and operation. Accordingly, the life of the lamps is compromised and the accuracy of any test is skewed. There is also no ability to calibrate the irradiance emitted from the lamps.

Various attempts have been made to improve on the above-noted drawbacks of the conventional testing apparatus shown in FIG. 1. Among these is an apparatus from Atlas Electric Devices Company, called Atlas Ci35 FADE-OMETER®; an apparatus from Heraeus called XENOTEST® 1200 CPS; U.S. patent to Suga, U.S. Pat. No. 4,544,995 issued Oct. 1, 1985; U.S. patent to Kockott, et al., U.S. Pat. No. 4,544,995 issued Apr. 27, 1971; and U.S. patent to Fedor et al., U.S. Pat. No. 5,206,518 issued Apr. 27, 1993.

The Atlas device is arranged for use with a xenon arc lamp and includes a closed loop irradiance monitor as its primary light control system. The monitor, using a light pipe, interference filter and photosensitive diode feeding into solid-state electronics, maintains predetermined irradiance levels and totalizes the energy received by the samples through an integrator. This device is also equipped with manual irradiance controls for use when periodically calibrating the system.

The apparatus from Heraeus is also directed for use with xenon arc lamps. This device employs three light detectors to detect the output of three individual xenon arc lamps.

A conventional apparatus including elements of these two above-discussed devices includes discharge lamps, which can be of a xenon type, that are vertically disposed. A filter surrounding the discharge lamps is provided to allow only desired wavelengths of light to pass. Sensors are provided to sense the output of the vertically positioned discharge lamps, and a rotating specimen holding rack is positioned to encircle the discharge lamps. Each of the detectors is provided to detect the irradiance produced from a respective discharge lamp over time. The rotating specimen holding rack rotates the specimens located in the specimen holding rack. The sensors are provided to track the output of the discharge lamps, and the rotating specimen holding rack attempts to provide each of the specimens with an average overall equal amount of irradiance. Inner walls are used to direct reflective light of the discharge lamps outward to the specimens.

Another device, employing ultraviolet lamps in an arrangement similar to FIG. 1, is known to include a single sensor. However, in such an arrangement it is necessary to match the characteristics of the lamps prior to placing them in such a device. This is required since the sensor will sense only the lamps closest to its location. Thus, the sensor will assume the lamps placed distant from it are operating the same as the lamps it actually senses.

The Suga patent attempted to improve on the prior art device shown in FIG. 1 by adjusting the alignment of the row of discharge lamps 10 of FIG. 1 into a nonsymmetric arrangement. The discharge lamps 10 are not disposed immediately below each other. Rather, they are in a specifically positioned arrangement. This was done in Suga in an attempt to provide irradiance to the samples 14 with a more uniform distribution.

The Kockott, et al. patent is directed to a device using an elongated source of irradiation inside a cylindrical carrier surface. Kockott, et al. discloses three approaches to provide a uniform distribution of irradiance to the samples. First, mirrors are arranged to reflect usable light; second, a light source is designed to increase light intensity at its ends; and, third, collimating discs are used to inhibit divergence of the radiation emitted from the source.

The Fedor et al. patent is directed to an apparatus similar in structure to the apparatus shown and described in FIG. 1 which has an improved light output controller and light beam distribution in the test chamber. Fedor et al. discloses an apparatus including a housing with a test chamber and a specimen supporting wall located inside of the chamber. A light source is provided in the test chamber. A ballast arrangement is connected to the light source for controlling the amount of power the light source receives from a power source. A controller is connected to the ballast arrangement, to produce a ballast control signal for controlling operation of the ballast arrangement according to a desired set-point value. A light source detector is disposed within the specimen supporting wall in order to detect irradiance existing in the test chamber so the light source detector can generate an irradiance signal, which is then input to the controller. The controller uses the irradiance signal to adjust the ballast control signal to maintain the selected set-point value. A calibration portion includes a reference detector inserted into the specimen supporting wall adjacent the light source detector, which is designed to detect the irradiance inside the test chamber and to produce a reference irradiance signal. The reference irradiance signal is transmitted to a calibration meter, which produces a calibration signal. The calibration signal is transmitted to the controller for calibrating the apparatus.

The Fedor apparatus also includes a barrier wall located within the test chamber. The barrier wall is configured to selectively block and divert beams of light produced by the arrays of light sources. The blocking and diversion of the beams occur in a pattern selected to increase an even distribution of the beams to the specimen supporting wall.

The Fedor apparatus still further includes a plurality of concurrently-operating, automatically-adjusted control channels for controlling output of the individual light sources. The channels control the output of at least one of the light sources.

While the above-discussed references provide some improvements upon the conventional apparatus discussed above, drawbacks still exist.

With particular attention to the Atlas and Heraeus devices, it is noted that both use a rotating specimen rack arrangement. This rack is necessary for a very basic reason. The Atlas device includes a monitoring system that monitors the overall output of the xenon arc lamp in order to attempt to maintain a predetermined total irradiance output level over time for the entire system. The Heraeus device uses three sensors to control the three different lamp's output over time. These sensor arrangements are used to produce an irradiance that is constant over time. However, neither of these devices use a sensing arrangement to make irradiance constant over space.

Both of the devices use a rotating specimen rack in an attempt to achieve spatial uniformity. Therefore, spatial uniformity is accomplished by having the specimens in the rotating rack revolve around the lamps, so the effective light dosage received by each specimen is an average of the different irradiances at each point on the circumference of the sample plane. Though rotating the rack increases uniformity, it also increases the complexity of the device by requiring a motor and associated rotation mechanisms.

Thus, even though these devices include irradiance sensing capabilities, they implement these capabilities only for a consistent output over time, not space. Due to the geometry of the devices, there is a different irradiance at every point around the circumference of the sample plane. Therefore, areas that are located in front of a discharge lamp will have a high irradiance area while samples that are at a position distant from a discharge lamp will receive lower irradiance. Rotation of the rack attempts to produce an overall average uniformity of irradiance impinging upon samples.

The known ultraviolet system using a single sensor includes the drawback of needing to match the lamps being used in the system. This requires extensive testing of the lamps prior to use. A further drawback is that in such a system, when a lamp located distant from the sensor location burns out or degrades, the decrease in its output will not be sensed. This is true as only the nearest lamps are actually sensed and an assumption is made that the remaining lamps are functioning in a similar manner.

The Suga patent attempts to increase the uniformity of light impinging upon specimens by moving the center two lamps away from the samples to increase uniformity of light to the samples from top to bottom. A drawback of such an arrangement is that it is not possible to easily retrofit existing weathering devices to gain whatever improvement there may be from the Suga arrangement.

A drawback to the Kockott, et al. patent is that it is directed to single lamp systems. Another drawback to Kockott, et al. is that it increases the complexity and cost of the apparatus.

A further drawback associated with the conventional testing apparatuses as discussed above is their calibration. These devices require manual manipulations by an operator, which in turn means the operator is required to make decisions that are critical to proper calibration. Since the operator is responsible for making decisions while manually re-calibrating the apparatus, the accuracy of the calibration will be dependent upon the skill of the operator. Additionally, since the calibration is accomplished manually, extended down time occurs during such calibration and there exists a substantial possibility of inaccuracies due to operator error.

The Fedor patent attempts to automate the control and calibration procedures for the testing apparatus. The control concurrently monitors a plurality of sensors disposed within the specimen supporting wall and controls each separate channel individually. To calibrate the individual sensors, the operator opens the door and installs a reference sensor within the specimen supporting wall inside the testing chamber immediately adjacent the individual sensor. The calibration procedure unfortunately introduces a great deal of operator error. The operator must manually select the type of lamp and the location for each calibration position. A disadvantage of this calibration procedure is that the operator must bypass the safety system which further introduces error into the reference sensor readings. Furthermore, the operator is exposed to harmful ultraviolet radiation.

Fedor also attempts to control the distribution of the light beams within the chamber by placing a barrier wall between the arrays of lamps. A drawback of such an arrangement is that the individual sensors and reference sensor are installed within the specimen supporting wall. In this location, the sensors are exposed to all of the weathering effects that are witnessed by the test specimens. Accordingly, the sensors deteriorate when used with this apparatus, thereby introducing error into the tests. Another drawback is the ballast used to control power to the lamps. Fedor discloses the use of only conventional ballasts, in which a signal is sent to the ballast to increase or decrease power from the ballast.

A still further drawback of the Fedor apparatus is the use of a concurrent control algorithm, which results in a biased sensor reading. As a result, the measured value of irradiance is inaccurate. Therefore, the control system has an error bias and the test results cannot be trusted as accurate.

Therefore, there is a need for an improved accelerated weathering apparatus that has an improved sensor location, unbiased sensor readings, improved control and calibration methodology and improved ballast construction and operation.

The subject invention contemplates a new and improved accelerated weathering apparatus that overcomes all of the above referenced problems and others and provides an easily operated, reliable testing structure.

BRIEF DESCRIPTION OF THE DRAWINGS

In the course of this detailed description, the reference will be frequently made to the attached drawings in which.

DETAILED DESCRIPTION OF A PREFERRED EMBODIMENT OF THE INVENTION

Figure 1:
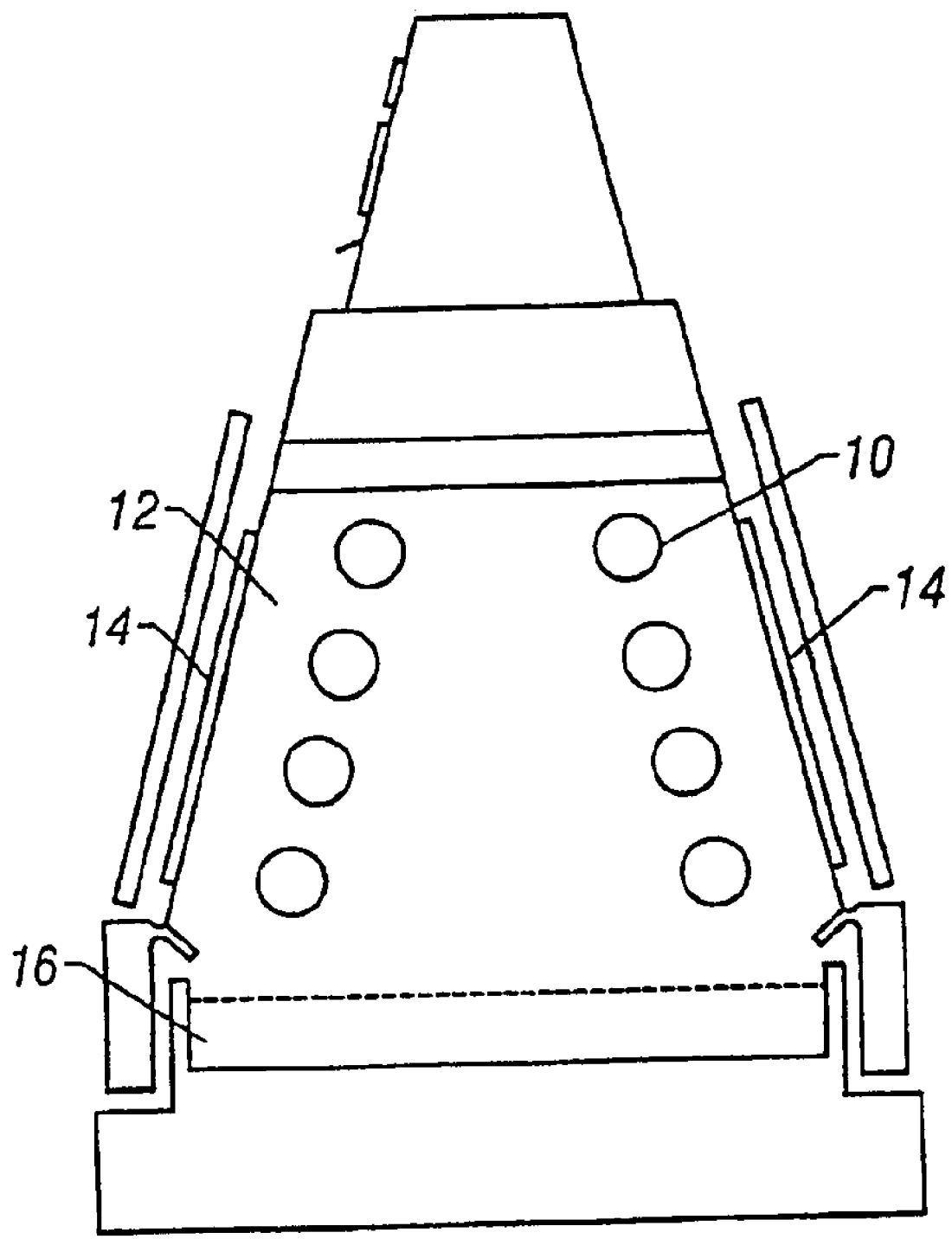
FIG. 1 is a conventional testing apparatus using discharge lamps in accordance with the prior art.
Figure 2A:
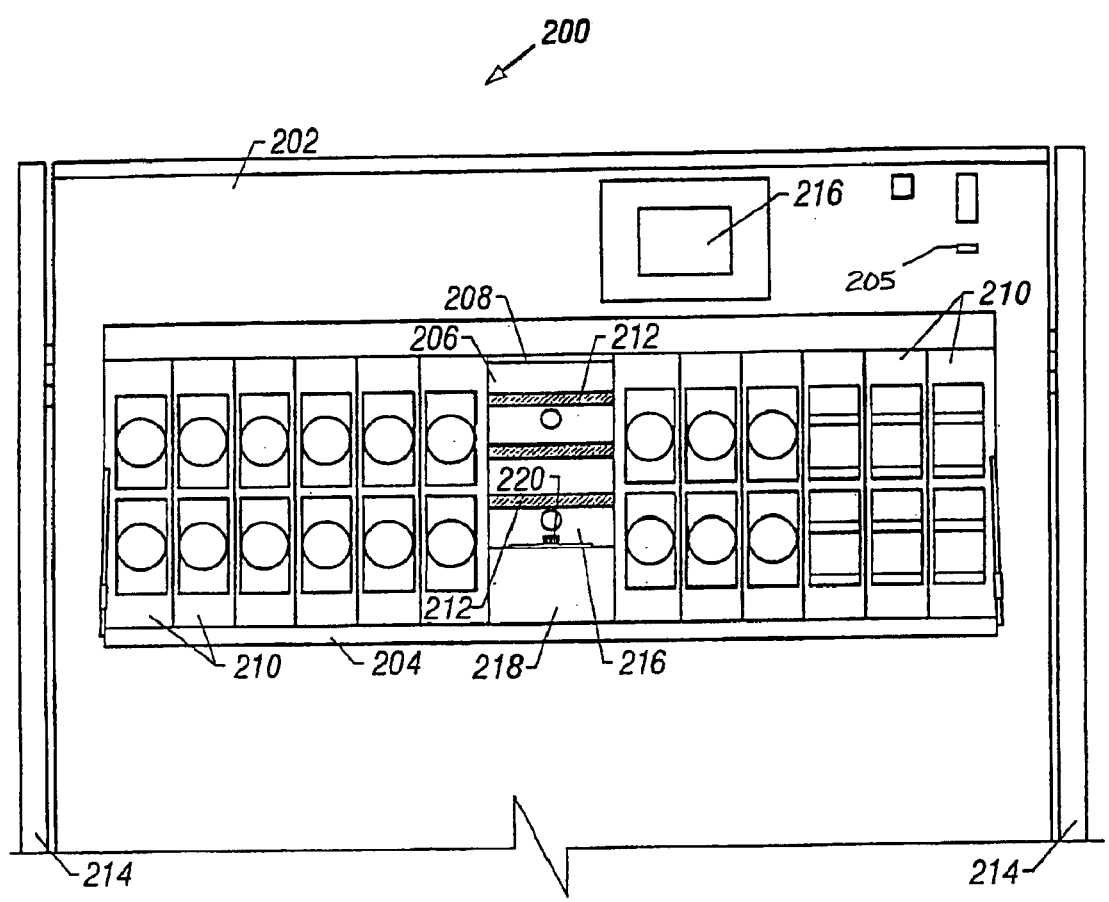
FIG. 2A is a partial front elevation view of an improved accelerated weather testing apparatus in accordance with the present invention.

FIG. 2A shows a partial front elevation view of an improved accelerated weather testing apparatus 200 in accordance with the present invention. The apparatus 200 includes an enclosure 202 having at least one door 204 for access to a test chamber 206 defined within the enclosure 202. Only one door 204 will be discussed herein. However, it will be recognized by those of skill in the art that another door disposed in opposition will be identical in form and function. The test chamber 206 is generally defined by a tank disposed within the enclosure 202. A specimen mounting apparatus 208 (best shown in FIG. 11) is disposed within the test chamber 206 for supporting specimen holders 210. A jack 205 is disposed on the enclosure 202 for interfacing with a plug to download data acquired and stored in the apparatus 200. The jack may be any structure which provides the desired interface characteristics. For example, a RS485, RS232 or any other suitable interface may be used.

In this embodiment, each specimen mounting apparatus 208 includes a top rail and a bottom rail collectively defining a specimen supporting wall. The bottom rail is located at a first or outer position in the tank adjacent the pivot point of the door 204. The top rail is located at a second or inner position in the tank away from the top of the door near the center of the chamber 206 such that the mounting apparatus is defined on a plane inclined to the vertical axis. The specimen holders 210 are positioned on each specimen supporting wall for exposure to light, heat and liquid in an accelerated weathering environment. The specimen holders 210 are aligned side-by-side on the specimen supporting wall in a substantially continuous manner. One specimen holder is not installed thereby creating an opening 216 along the specimen supporting wall which cooperates with a pocket 218 formed in the door 204. Accordingly, when the door 204 is closed, sensors 220 mounted in the pocket 218 are exposed to the light source 212 for accurate irradiance detection.

A light source 212 is disposed within the test chamber 206 for producing light in the test chamber 206. In this embodiment, the light source 212 is shown as a plurality or array of lamps. In this embodiment, the plurality of lamps are disposed in first and second rows, each having four lamps. It will be recognized by those of skill in the art that the arrangement, configuration and number of lamps may be altered without departing from the present invention. The light source 212 is selected from the group of lamps that generate ultraviolet light in the UV-A, UV-B and UV-C ranges. For example, the lamps may be fluorescent, xenon or any other suitable type of lamp.

A power source (not shown, see FIG. 3) powers the light source 212. For example, the power source may include standard commonly available 110V or 120V, single phase power or any other suitable power source such as 220V, 240V, 440V, multiphase power as required. Protection exterior doors 214 may also be provided in connection with the enclosure 202 to protect the enclosure 202 during lengthy test procedures. A control panel 216 provides an operator interface with the operating system as will be discussed in further detail below.

Figure 2B:
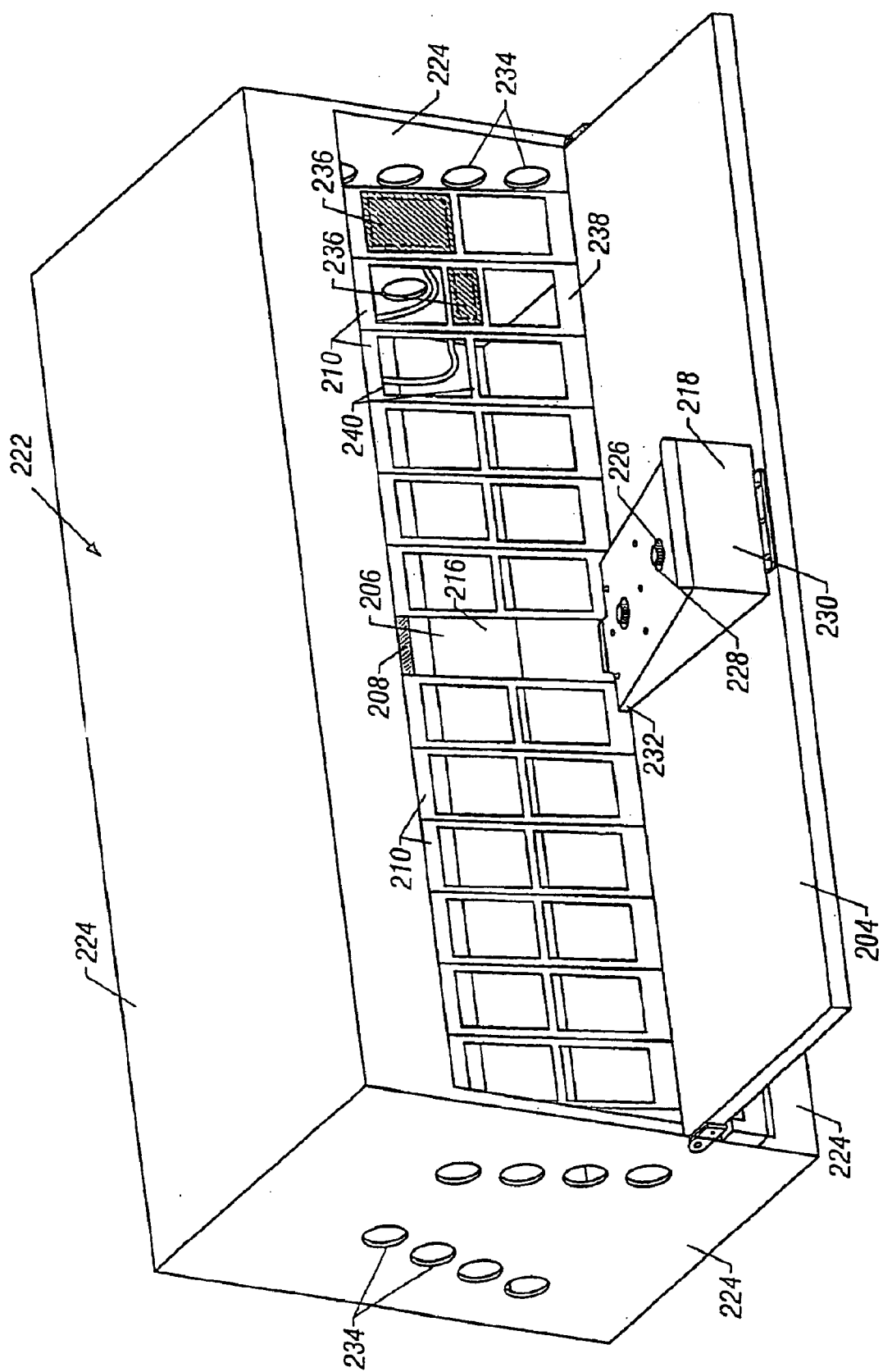
FIG. 2B is a detailed perspective view of a tank portion of the accelerated weather testing apparatus of FIG. 2A.

FIG. 2B is a detailed perspective view of the tank portion 222 of the accelerated weathering testing apparatus of FIG. 2A. The tank portion 222 is a cabinet-style enclosure with a pair of doors 204 on opposing sides defining an interior test chamber 206. A light source is disposed within the test chamber 206 and a power source powers the light source 206 as discussed above and will be described in detail below. The tank portion 222 further includes an internal frame and exterior mounted panels 224.

A first door 204 is pivotally mounted to opposing side panels 224 and is in opposition to the second door (not shown), which is pivotally mounted to the side panels 224.

As shown, only the first door 204 is illustrated, the second door is identical in structure and function. Accordingly, only the first door 204 will be discussed below. The door 204 provides access to the test chamber 206. A recessed pocket 218 is formed in the door 204 in a generally medial location such that a recess is provided on the exterior surface of the door 204 so that a test module (not shown, but described in detail below) and calibration module (not shown, but described in detail below) may each be interchangeably, removably disposed within the pocket (as will be discussed in further detail below). A pair of vertically aligned test modules (not shown, but described in detail below) are removably disposed in each pocket 218 for detecting irradiance in the test chamber 206 produced by the light source and generating an irradiance signal representative of the detected irradiance, so that the test modules are not the harsh environment of the test chamber.

The test modules (not shown, but described in detail below) include a test sensor 226 which is inserted into an aperture 228 formed in the pocket 218 at a location corresponding to the light source to detect irradiance in the test chamber 206 produced by the light source. The test modules are arranged to detect different spatial areas of five specimen mounting apparatus. The test sensors can take any form well known in the art such as, for example, an optical photodiode.

The floor of the pocket 218 is inclined to the door 204 and defined in a plane parallel to the plane defining the specimen supporting wall. As a result, the floor of the pocket 218 is immediately adjacent to the specimen supporting wall and specimen holders 210 disposed thereon; however, there is no contact between the pocket 218 and the specimen mounting apparatus 208, or specimen holders 210. When the door is closed, the inclined floor of the pocket 218 locates the sensor 226 equally between adjacent lamps and within the mounting apparatus opening 216. However, it will be noted that this configuration may be modified such that the pocket 218 may be offset to one side or the other as necessarily required by the structure of the remainder of the accelerated weathering testing apparatus. The shape, depth and contour of the pocket 218 preferably corresponds to the configuration of the lamps in the test chamber.

One test sensor 226 per pair of lamps provides accurate irradiance detection in accordance with the present invention. The pocket 218 is shown to have a generally triangular shape when viewed from the side, such that the back 230 of the pocket 218 is disposed away from the pivot of the door 204 and extends into the test chamber farther than the front 232 of the pocket 218 adjacent the pivot of the door. The test sensor 226 includes a standoff or projecting portion and an input, which are used as a light pipe for transferring lamp irradiance to the test module mounted outside the test chamber 206 in the pocket 218 of the door 204. The test sensor 226 may also include an optical filter which permits passage of light having a certain wave-length. The door 204 has a small handle at the top to aid in opening and closing.

The tank 222 defines the test chamber 206 where the environment can be manipulated by introduction of light, heat, and moisture. The plurality of apertures 234 in the end panel 224 of the tank 222 are for the lamps. Similarly, a plurality of apertures is present in the opposing end panel of the tank. Electrical connections for the lamps are made outside the test chamber to avoid any corrosion that would introduce error into the control system resulting in inaccurate test results.

A temperature sensor 236 generates a temperature signal representative of the temperature within the test chamber 206 and transmits the temperature signal to a controller (discussed in detail below) in order to maintain the desired irradiance within the test chamber 206. The temperature sensor 236 may be configured to replace a specimen on a specimen holder 210 or alternatively a smaller version may be used. The smaller version requires an alternative specimen holder 238 where the temperature sensor 236 is disposed between two specimen apertures 240. It will be recognized by those of skill in the art that any suitable sensor configuration may be used to generate a temperature signal. In this embodiment, the temperature sensors are black body sensors which generate a signal responsive to the temperature within the test chamber 206.

Figure 3:
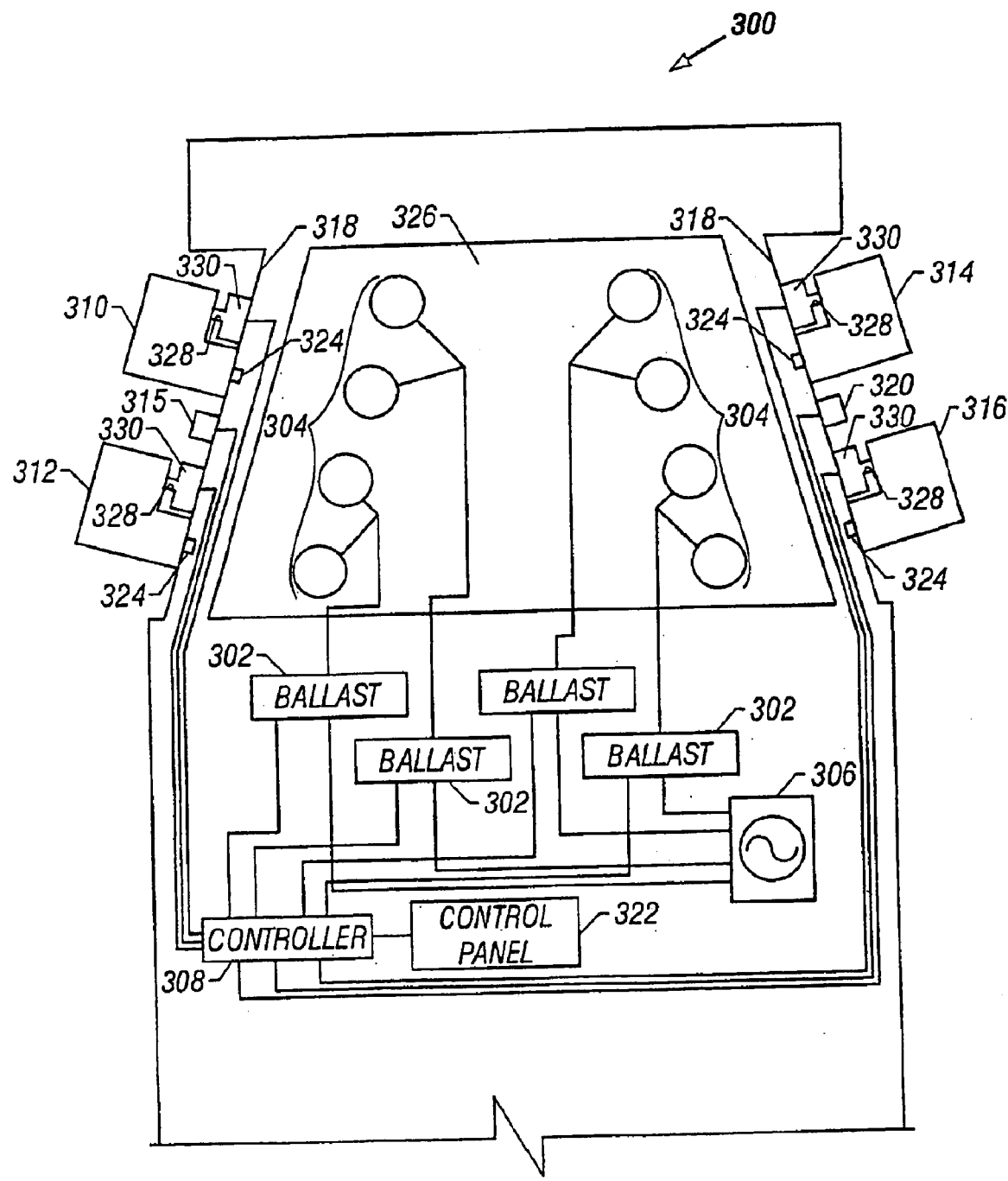
FIG. 3 is a diagrammatic illustration end view of the accelerated weather testing apparatus showing the features of the control channels in accordance with the present invention.

FIG. 3 shows a diagrammatic illustration and view of the accelerated weathering testing apparatus showing the features of the plurality of automatically adjustable control channels in accordance with the present invention to sequentially control output of the array of light sources. In this embodiment, each of the four separately adjustable control channels includes a ballast 302, each of which functions identically, and thus only one will be discussed, four test modules 310, 312, 314 or 316 and a controller 308. The test modules 310, 312, 314 and 316 each include a plug 328 which interfaces with a receptacle 330 disposed in the pocket 318 in order to connect the controller 308 and the test modules 310, 312, 314 or 316 such that the controller 308 is automatically connected to the test module 310, 312, 314 or 316 when the test module 310, 312, 314 or 316 is disposed within the pocket 318.

Each ballast 302 is connected to at least one of a plurality of light sources 304 for controlling the amount of power received by the light source 304 from a power source 306. The control channel also includes a controller 308 connected to the test modules 310, 312, 314 and 316, the temperature sensors 318 and 320, the control panel 322 and the ballasts 302 for generating a ballast control signal, which controls operation of each ballast 302.

A test sensor 324 included with each of the test modules 310, 312, 314 and 316 has a linear slope of responsivity in the ultraviolet range to detect irradiance in a test chamber 326. The test modules 310, 312, 314 and 316 generate an irradiance signal representative of the detected irradiance produced by the plurality of light sources 304 which is transmitted by a transmitting device disposed within the test module 310, 312, 314 or 316 to the controller 308. In this embodiment, the test module 310, 312, 314 or 316 amplifies and filters the irradiance signal to reduce frequency noise. It will be recognized by one of skill in the art that this may be accomplished by any of a variety of means. For example, reduction in frequency noise may be achieved by converting a high impedance signal to a low impedance signal with gain or any other suitable method. The irradiance signal is then transmitted to the controller 308 such that the controller 308 may periodically adjust the ballast control signal to maintain the irradiance signal at a desired set point. The controller 308 may alternatively, or additionally, include software to perform some or all of these functions. The ballast control signal may also be adjusted by the controller 308 based upon the current draw of the ballast.

The ballast control signal is initially based upon a set point entered by an operator which represents a desired irradiance within the test chamber. In operation, the controller 308 outputs a ballast control signal to the ballast 302 based on the set-point. The test module 310, 312, 314 or 316 senses the irradiance from adjacent light sources and transmits the irradiance signal to the controller 308. The controller 308 receives the irradiance signal from at least one of the test modules 310, 312, 314 or 316. The controller 308 then adjusts the respective ballast control signal based upon the gain between the ballast control signal and the irradiance signal. The controller 308 then outputs the adjusted ballast control signal. The above steps are then repeated for the next test module 310, 312, 314 or 316 in sequence for the desired period of time. In another embodiment, the temperature sensor 318 transmits a temperature signal to the controller 308. The controller 308 then further adjusts the respective ballast control signal based upon the temperature signal.

The ballast 302 contains circuitry that, at start up, applies a low voltage to the light source 304 for a desired period of time in order to warm the light source 304 before ignition. This minimizes the shock to the light source 304, thereby prolonging its life and reducing expenses. By way of example, the desired period of time may be approximately 1.5 seconds, and the low voltage may be between 2 and 5 volts, but one of ordinary skill in the art could use other values. Moreover, even after the light source 304 is warmed an ignition pulse is applied to the light source 304. Preferably, the ignition pulse is approximately in the range of four hundred volts. Then, the low voltage is ramped to the full operating voltage of the light source 304 and pulled back to the set point operating voltage rather than immediately increased to that level, further minimizing the shock to the light source 304. The ballast 302 may instead, or additionally, include software to perform some or all of these functions.

Lamp performance depends on several factors, including temperature of environment, current, voltage, etc. In order to optimize performance of the light source 304, these factors must be taken into consideration. The present invention considers those above factors by measuring and inputting these variables into the control system such that the system may be optimized by gain factors. As a result, the life of the light source 304 is improved. By monitoring these variables the irradiance of the light source 304 may be controlled independently of the sensors, or alternatively in cooperation with the sensors as a dual feed back mechanism. This is particularly advantageous with regard to predicting life of a light source 304 bulb.

Figure 4:
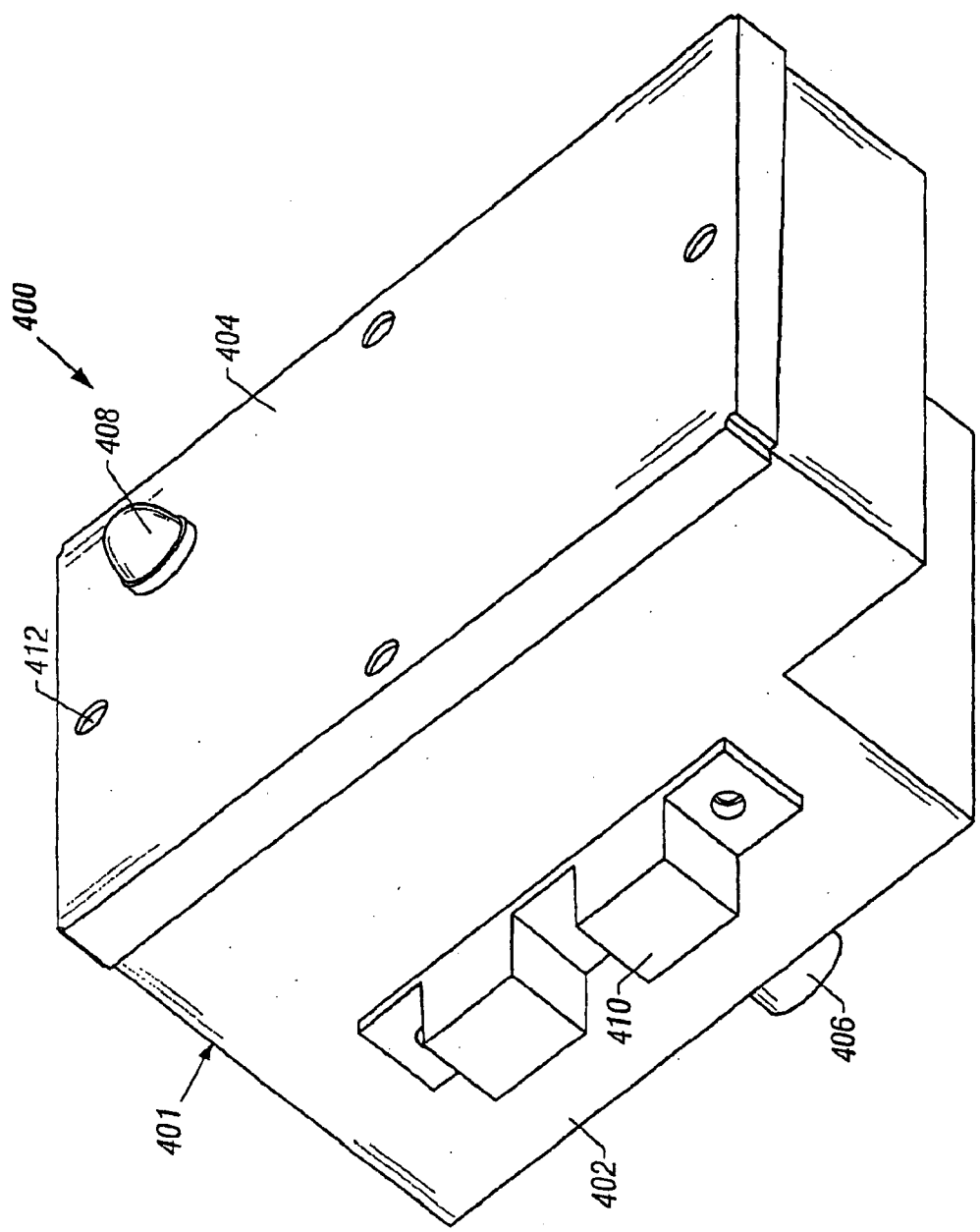
FIG. 4 is a top perspective view of a test module in accordance with the present invention.

FIG. 4 is a top perspective view of a test module 400. The test module 400 includes a housing 401 having a main body portion 402, a cap 404, a projecting portion 406, an indicator element 408, and mounting apparatus 410. A high-density connector element (not shown in this view) is also included. The housing 401 is substantially hollow permitting mounting of the test sensor and associated electronics. The projecting portion 406 extends through an aperture in the bottom of the housing. The projecting portion 406 functions as a light pipe as is known in the art to channel the light from the chamber to the test sensor in order to generate an irradiance signal. The cap 404 is secured to the main body portion 402 by a plurality of threaded fasteners 412. It will be recognized by those of skill in the art that any other suitable fastening method may be used. The indicator element 408 shows that the sensor module is properly installed and operating. The mounting apparatus 410 includes a pair of substantially U-shaped elements disposed on each side of the housing 401 to engage projections disposed on the floor of the pocket in a snap-fit manner. A printed circuit board (not shown) is provided with various electronic components mounted thereon for amplifying and filtering the signal generated by the test sensor and for transmitting the signal to the system controller. The amplification and filtering of the irradiance signal has the purpose and effect of reducing high frequency noise. This can be achieved in many ways well known in the art including, for example, converting a high impedance signal to a low impedance signal with gain. A plurality of threaded fasteners (not shown) may be used to secure the various different parts of the sensor together. Other construction and assembly methods and devices may also be used.

Figure 5:
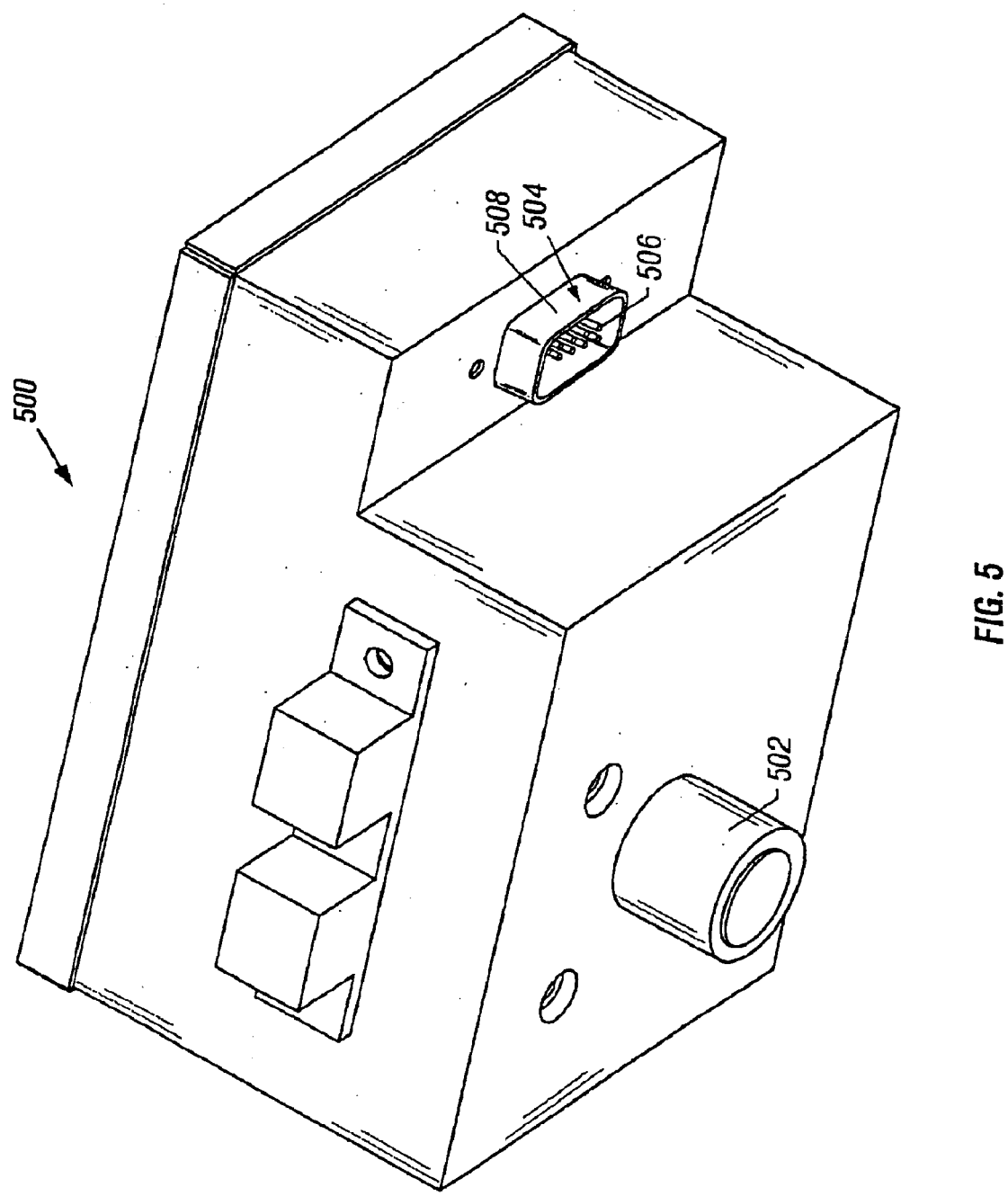
FIG. 5 is a bottom perspective view of the test module in accordance with the present invention.

FIG. 5 shows a bottom perspective view of the test module 500 of FIG. 4. The projecting portion 502 and connector element 504 are shown. The high-density connector element 504 has a plurality of pins 506 and a grounding shield 508. The connector element 504 provides an interface between the sensor module 500 and the system controller. The cable (not shown) for such interface may then be securely and safely mounted within the door providing a clean installation that is durable and not affected by the harsh environment of the test chamber, nor by ill handling from operators.

Figure 6:
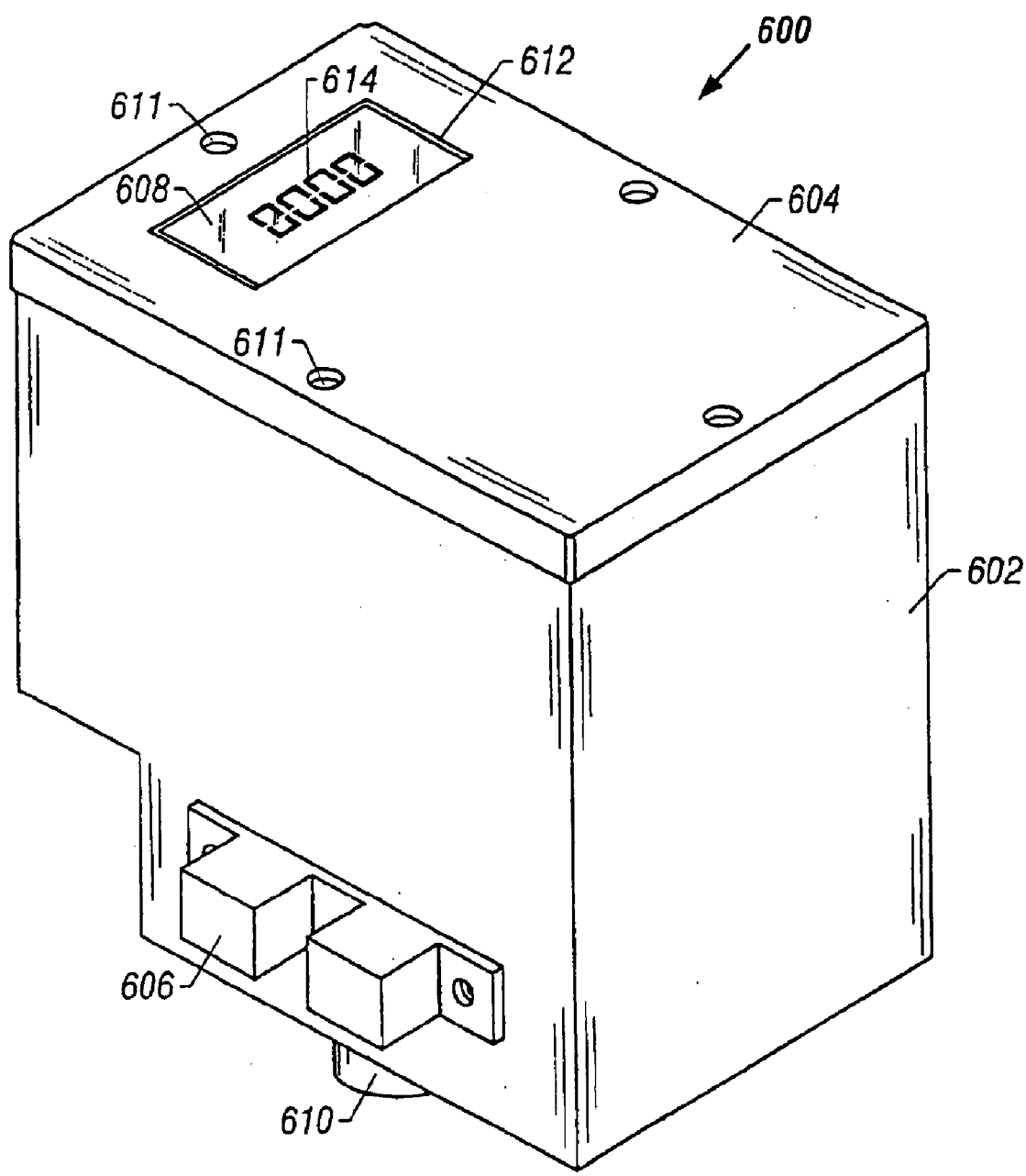
FIG. 6 is a top perspective view of a calibration module in accordance with the present invention.

FIG. 6 shows the calibration module 600, which includes a main body portion 602, a cap 604, mounting elements 606, a display 608, projecting portion 610, a reference sensor (not shown), and a high density connector (not shown). The calibration module 600 detects the irradiance in the test chamber in order to generate and display a reference valve 614 which represents the detected irradiance. The calibration module 600 interchangeably replaces the test module in the pocket.

The cap 604 is secured to the main body 602 by a plurality of fasteners 611 and has an aperture 612 through which the display 608 may be viewed. The display 608 generates a numeric image 614 in response to a signal from the reference sensor disposed within the housing. The numeric image 614 is a reference value representative of the irradiance detected by the reference sensor. An operator inputs the reference value to the controller for adjusting the ballast control signal. The mounting elements 606 are U-shaped and disposed on opposing sides of the main body 602 to engage projections disposed on the floor of the pocket in a snap-fit manner. The structure and function are the same as the mounting elements on the test module in FIGS. 4 and 5.

The display 608 has a plurality of pins which engage a printed circuit board in order to be responsive to signals generated by the reference sensor and associated electronics. The sensor is in communication with the printed circuit board, the circuit, and components thereon in order to generate a signal representative of the irradiance detected from the adjacent bulbs in the test chamber. The calibration module 600 includes at least two internal calibration routines which allow calibration of at least two different types of ultraviolet light while using the same calibration module. The calibration module 600 also may include internal routines that automatically calibrate for the group of lamps that generate ultraviolet light in the UV-A, UV-B or UV-C ranges.

Figure 7:
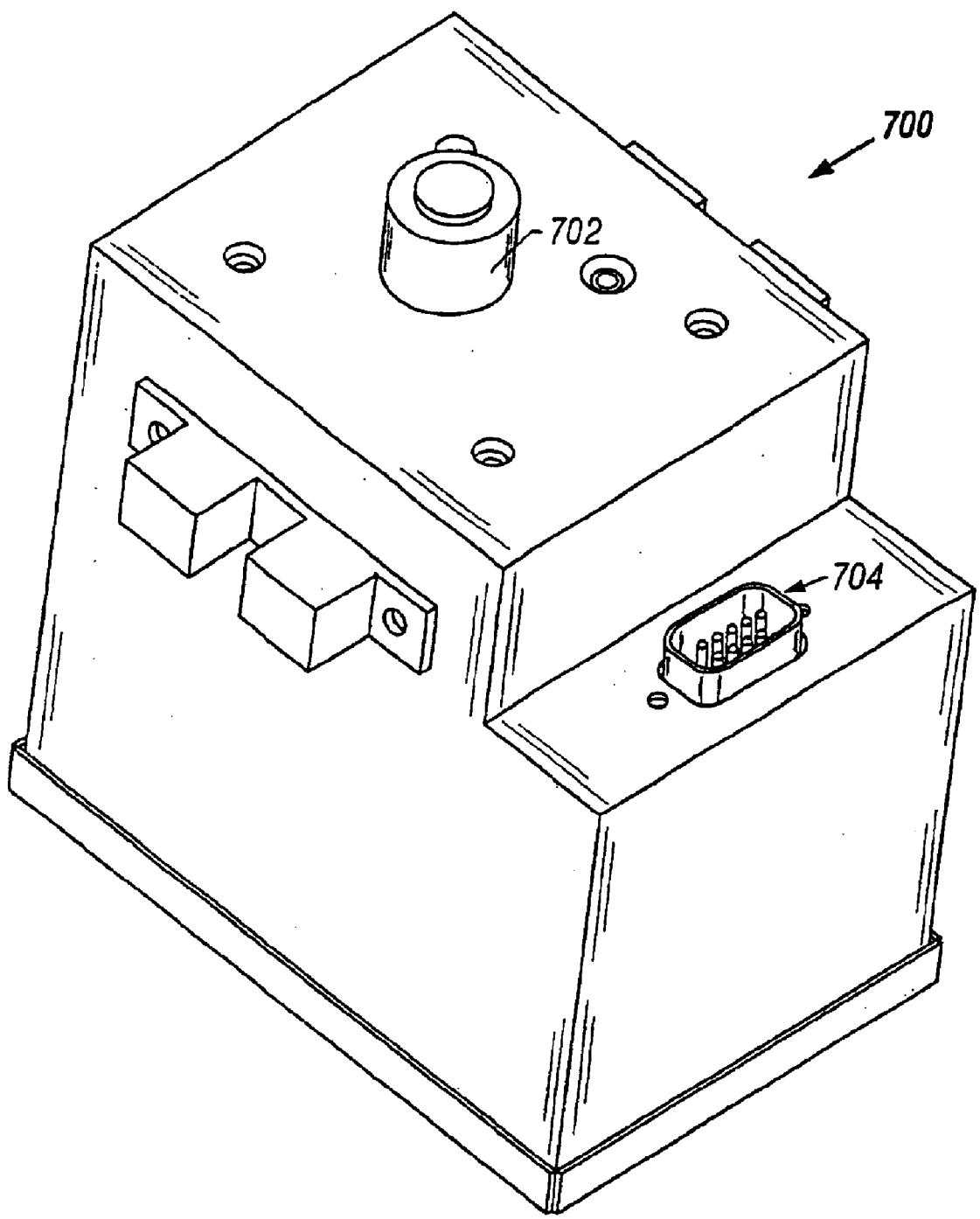
FIG. 7 is a bottom perspective view of the calibration module in accordance with the present invention.

FIG. 7 shows a bottom perspective view of the calibration module 700 of FIG. 6 in which the projecting portion 702 and high-density connector 704 are shown. The projecting portion 702 has a structure and function similar to the test module projecting portion which includes operating as a light pipe, as is known in the art, to protect the reference sensor from the harsh environment of the test chamber. Likewise, the high-density connector 704 interfaces with the same high-density receptacle disposed within the door pocket as the test module. The connection with the system controller confirms that the calibration module 700 is in the proper calibration location and that the type of ultraviolet irradiance being detected, i.e., UVA, UVB, or UVC is confirmed. The calibration module 700 may instead, or additionally, include software to perform some or all of these functions. The calibration sensor (not shown) does not automatically forward the reference signal generated by the reference sensor to the system controller; rather, the value is outputted only to the display for observation and manual notation by the operator. The reference sensor of any suitable type may be used to perform its function. For example, the reference sensor may be an optical photodiode type or any other suitable sensor. Operation of the calibration module and calibration procedure will be discussed in detail below.

Figure 8:
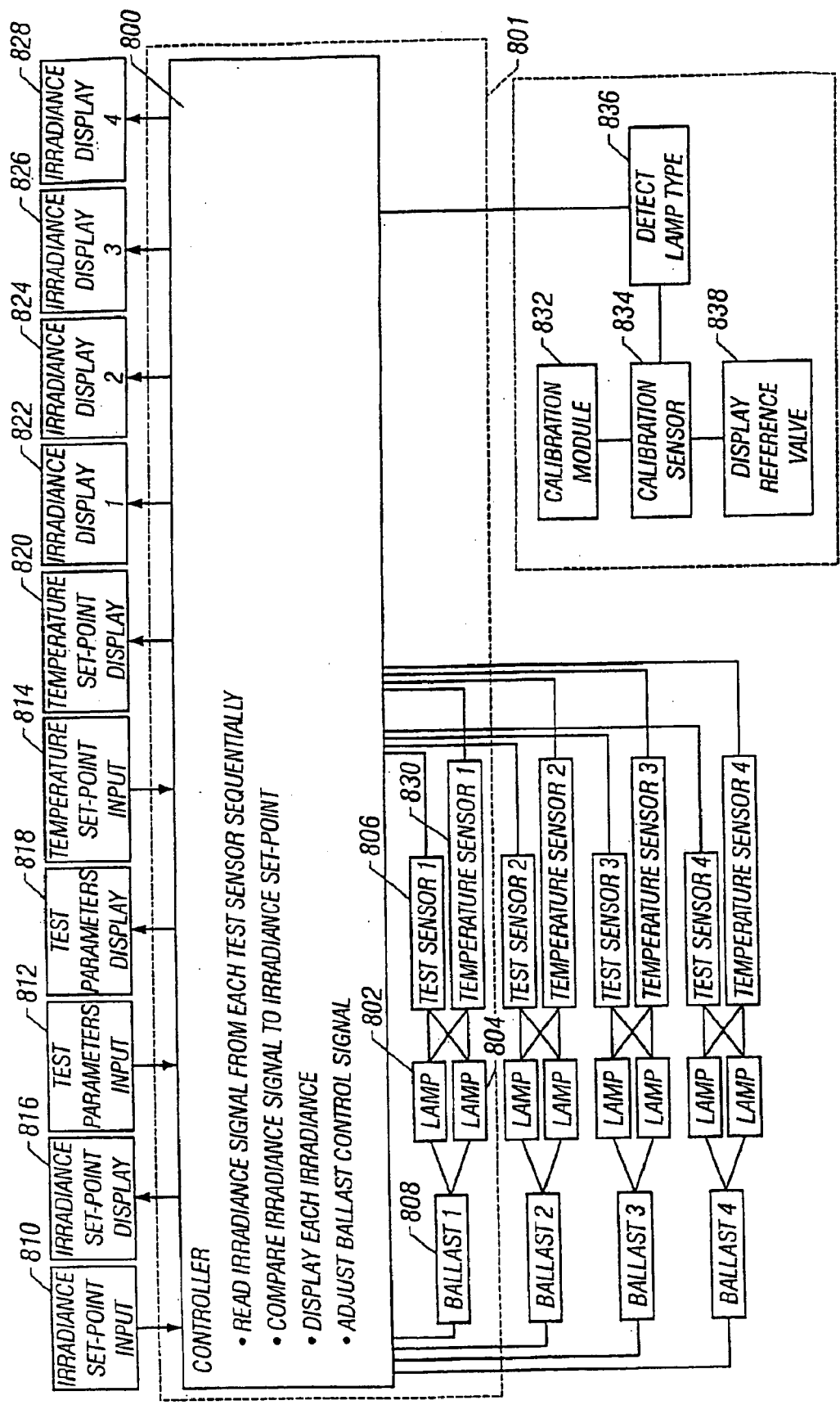
FIG. 8 is a flow chart diagram showing the sequential control for light sensor modules in accordance with the present invention.

FIG. 8 shows a block diagram for the sequential control of four test modules in connection with the accelerated weathering testing apparatus. The controller 800 may be any suitable device, such as a programmable logic controller (PLC) or other suitable device which may be used as the main system controller for the operation of the testing unit, including monitoring and controlling irradiance, calibration of the controller, and the operation of various different weathering tests on a plurality of automatically adjustable control channels for sequentially controlling output of the light sources. The controller 800 automatically detects the difference between a test module and a calibration module.

The control channel 801 algorithm or sequence for one channel will be discussed as the remaining control channels are similar and follow the same procedure. The control channel includes a pair of lamps 802, 804 and a test module including a test sensor 806 and a transmitting device, and a ballast 808. Each control channel is adjusted continuously in a sequential manner for a desired number of cycles. For example, the first control channel 801 is adjusted, then the controller movers to the second control channel and makes an adjustment, then the controller moves to the third control channel and makes an adjustment, then the controller moves to the fourth control channel and makes an adjustment, thereby defining a test cycle. The controller 800 then begins the sequential adjustment over again for the desired number of cycles.

In operation, the irradiance set point 810, test parameters 812 and temperature set-point 814 are input to the controller 800 by an operator via the user interface. The user interface may be any suitable display and data entry device. For example, the user interface may be a touch-screen or any other suitable device. The user interface displays the irradiance set point 816, test parameters display 818, temperature set-point 820 and the irradiance detected for each of the four control channels in this embodiment 822, 824, 826 and 828 at selected times and on certain screens of the user interface as will be described in detail below.

The controller 800 then begins the test procedure according to the test parameters 812. Again, only the first control channel 801 will be discussed as each other control channel functions in the same manner. The irradiance set point 810 establishes the initial ballast control signal which is transmitted from the controller 800 to ballast 808, to set the amount of current received by the lamps 802, 804.

The test module test sensor 806 detects the irradiance at its position from the adjacent lamps, generates and transmits an irradiance signal to a proportional integrator derivative (PID) module within the controller so that the irradiance signal may be compared to the desired set point 810 input into the controller 800. The gain is the measurement of error between the set point 810 and actual irradiance signal generated by the test sensor 906. An updated ballast control signal from the proportional integrated derivative module of the controller based upon the gain value is transmitted to the ballast 808 for adjusting the irradiance output of a pair of lamps 802, 804 in parallel. The controller 800 then moves to the next control channel to detect the irradiance, compare against the set point, provide a corrected ballast control signal, and adjust the irradiance. This process is sequentially and repeatedly enacted such that precise control of the irradiance for each control channel is maintained.

An additional input may be provided in each control channel algorithm or sequence. A temperature sensor 830 mounted on a black body panel disposed within the test chamber, in a manner similar to how a specimen is mounted as discussed above, is responsive to changes in temperature, generates a temperature signal and transmits the temperature signal to the controller 800 for adjusting the heater to maintain a desired temperature within the test chamber. The heater control signal is adjusted after comparing the irradiance signal to the irradiance set point and determining the gain. The PID updates the heater control signal from the controller based upon the temperature gain value. In an alternate embodiment, the temperature sensor 830 may be mounted on a specimen holder between specimens as discussed above. In another alternative embodiment, the temperature signal may be transmitted to the controller 800 for adjusting the ballast control signal in order to maintain a desired irradiance within the test chamber. In this alternative embodiment, the ballast control signal is adjusted after comparing the temperature signal to the temperature set point and determining the gain. The PID updates the ballast control signal from the controller based upon the temperature gain value. The temperature signal and set point provides an additional level of control over the irradiance output. It is known that as the temperature of the lamp increases, the irradiance decreases. It is also well known that the resistance of materials can be dependent on their temperature. Thus, when the lamp set point is at maximum power at a low temperature, conventional prior art apparatus cannot compensate for an increase in temperature. However, by using the above method of temperature compensation, the lamp may be overdriven to compensate for changes in the temperature and increase the life of the lamp. The ballast controls the irradiance output of the lamps in response to the ballast control signal.

Upon start up of a testing sequence, the ballast preheats the light filaments for approximately one and one half seconds using a very low voltage, preferably two to three volts. Next, an ignition pulse is applied to the light filament in the range of approximately four hundred volts. The voltage is then ramped up gradually until lamp output goes to full. The operating voltage is then dropped to the desired set point. This voltage is maintained constant during the testing sequence. Current for the lamps is relatively low at 430 mA at 100 volts AC. The crest factor is less than 1.2. The lamp status, namely voltage and current, is obtained by a five percent (5%) monitoring coil on the output transformer. The ballast control signal voltage range is from 0 to 10 volts DC. Ten volts to 2 volts controls 10% to 100% lamp output, while control voltage of 0 to 2 volts controls 130% to 100% lamp output. When the filament resistance decreases, due to temperature change, the ballast maintains constant current without loading at an output voltage at 70° C. lamp temperature. The dimming function is also provided using a voltage to frequency converter. By increasing the frequency, the lamps dim and decreasing the frequency, brightens the lamps or vice versa as desired.

The calibration module 832 includes a calibration or reference sensor 834 which detects the type of lamp 836 and generates and displays a reference value 838. The calibration algorithm, or sequence, will be discussed in detail below.

Figure 9A:
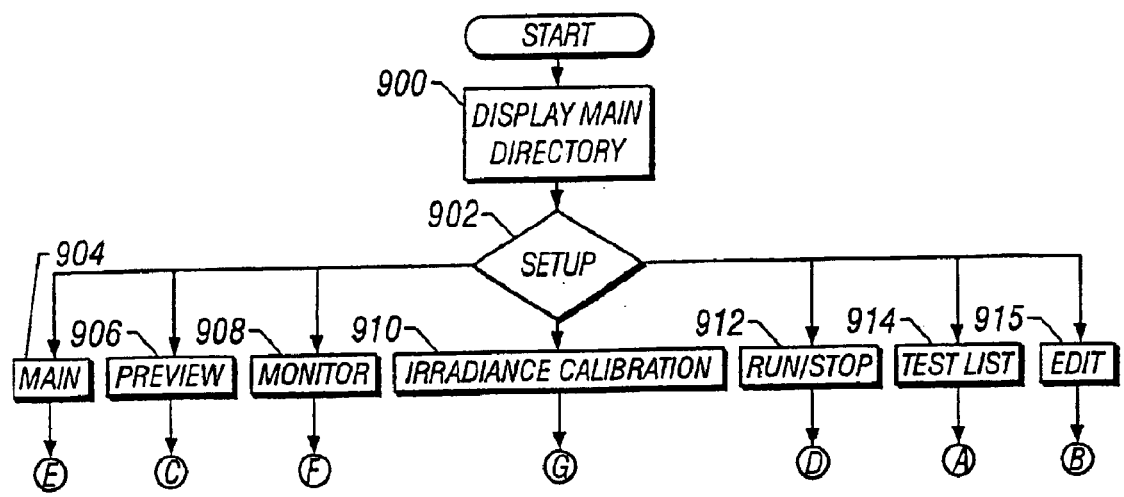
FIGS. 9A–H are flowcharts illustrating operation of the system controller user interface in accordance with the present invention.

FIGS. 9A–9H show flowcharts illustrating operation of the controller user interface. In FIG. 9A, at block 900 a main directory is displayed from which the operator can reach any other subroutine screen of the user interface by pressing the appropriate navigational button at decision block 902. The navigational buttons access the following subroutine screens: main 904, preview 906, monitor 908, radiance calibration 910, run/stop 912, test list 914, and edit 915.

Figure 9B:
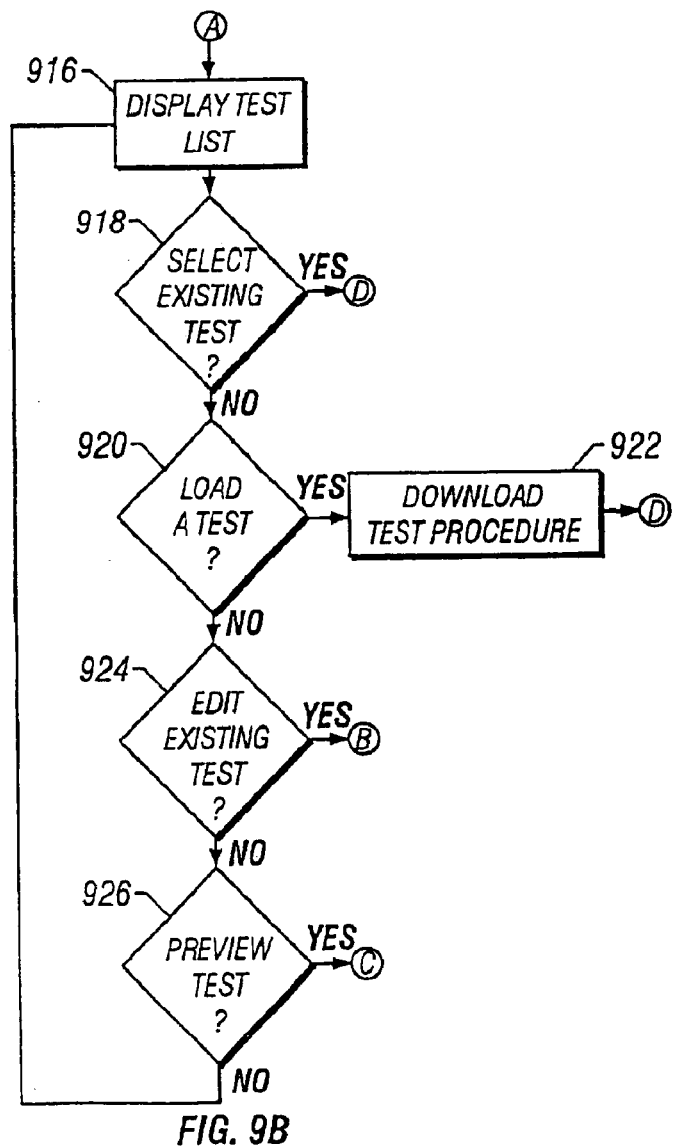

FIG. 9B is a flowchart illustrating the operation of the test list screen, which allows an operator to load an established, pre-existing test into the run memory or to preview any test. Each test has a different set of parameters that correspond to the materials and environment being tested. Various parameters may include, but are not limited to, intensity of irradiance, cycle time, moisture, and temperature.

At block 916, the list of available tests is provided to the operator. At decision block 918 the operator chooses whether to select an existing test. If yes, the operator proceeds to FIG. 9E describing run/stop screen, which will be discussed below with respect to that figure. If no, the system proceeds to decision block 920 where the operator decides whether to load a test. If yes, then the system proceeds to block 922 where that test procedure is downloaded and then implemented by way of the run/stop screen to be discussed with respect to FIG. 9E below. If at decision block 920 the operator chooses not to load a test, then the system proceeds to decision block 924 where the operator decides whether to edit the existing test. If yes, then the system proceeds to the edit screen, which will be discussed with respect to FIG. 9C below. If no, then the system proceeds to decision block 926 where the operator decides whether to preview a test. If yes, then the system proceeds to the preview screen, which will be discussed with respect to FIG. 9D below. If no, then the system returns to block 916 where the test list is displayed and this procedure begins anew.

Figure 9C:
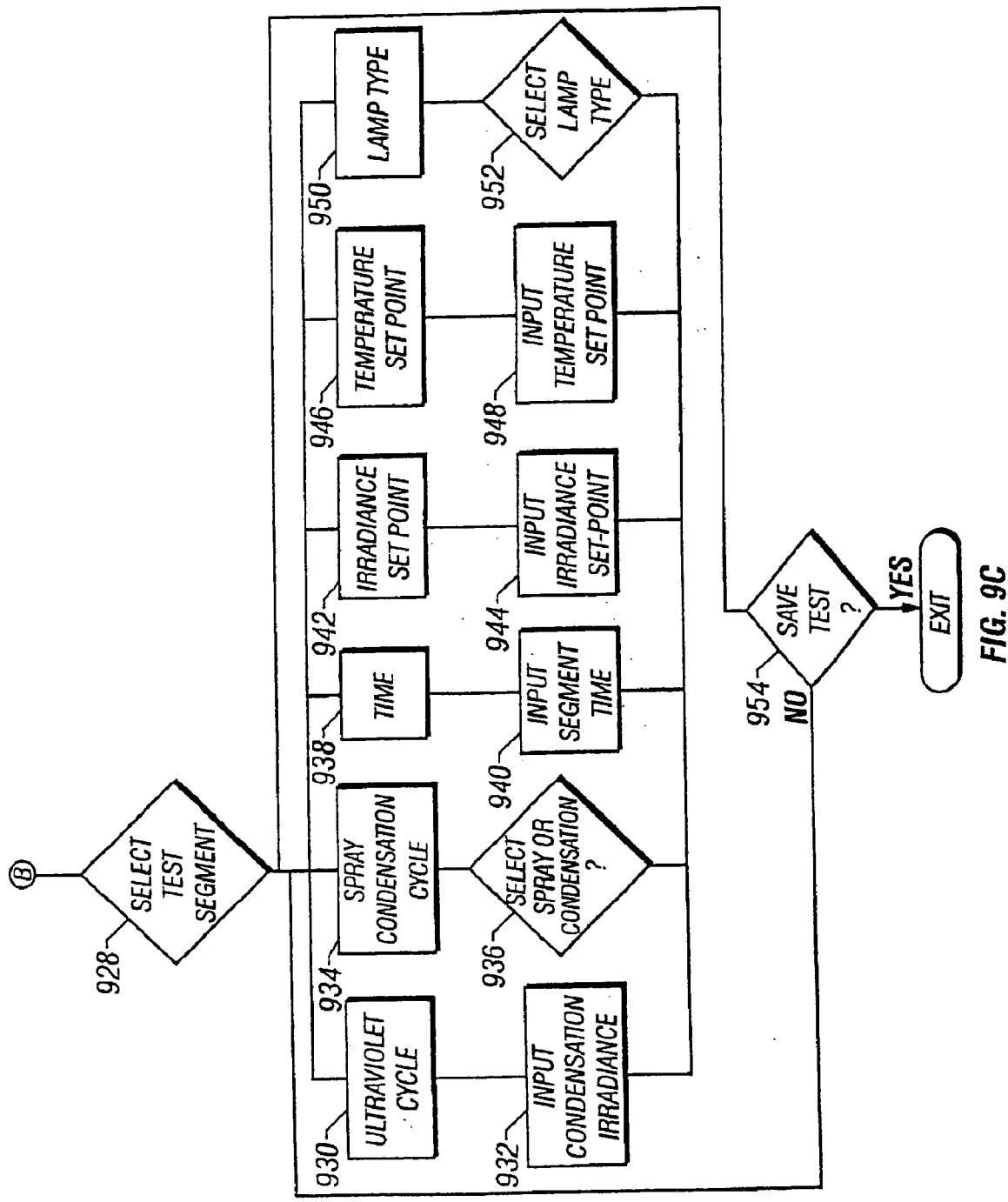

FIG. 9C is a flowchart illustrating the operation of the edit screen. The edit screen is responsive to the edit button 915 on the main directory display 900 and the test list screen, block 924, and allows an operator to create a new test or edit some test parameters in any existing test. For example, the operator can choose the type of lamp to be used during the test or any segment parameters, such as the type of ultraviolet light, water spray or condensation cycle, segment time, ultraviolet irradiance set point, and temperature set point. At decision block 928, the operator selects the test segment to be edited. Block 930 represents the selection of the ultraviolet cycle, which allows the operator to input the concentration of irradiance at block 932. Block 934 represents the spray condensation cycle, which allows the operator at decision block 936 to select either spray or condensation. Block 938 represents the selection of a time segment, which allows the user at block 940 to input segment time. Block 942 represents the selection of the irradiance set point, which allows the operator at block 944 to input the irradiance set point. Block 946 represents a selection of the temperature set point, which allows the user at block 948 to input the temperature set point. Block 950 represents the selection of a lamp type, which allows the user at decision block 952 to select which of an available number of lamp types to use in the test segment. At decision block 928, regardless of whether the user selects to change any of the parameters represented by blocks 930–952, the operator can proceed to decision block 954 where the operator may choose to save the test (i.e., the collection of parameter values). If no, then the system returns to decision block 928. If yes, then the system saves the test parameters and returns to the display main directory at block 900.

Figure 9E:
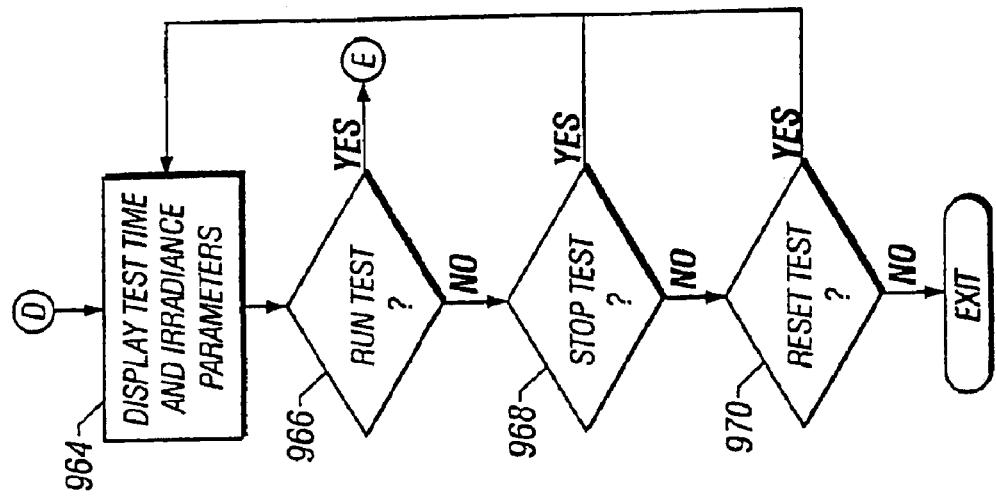
Figure 9D:
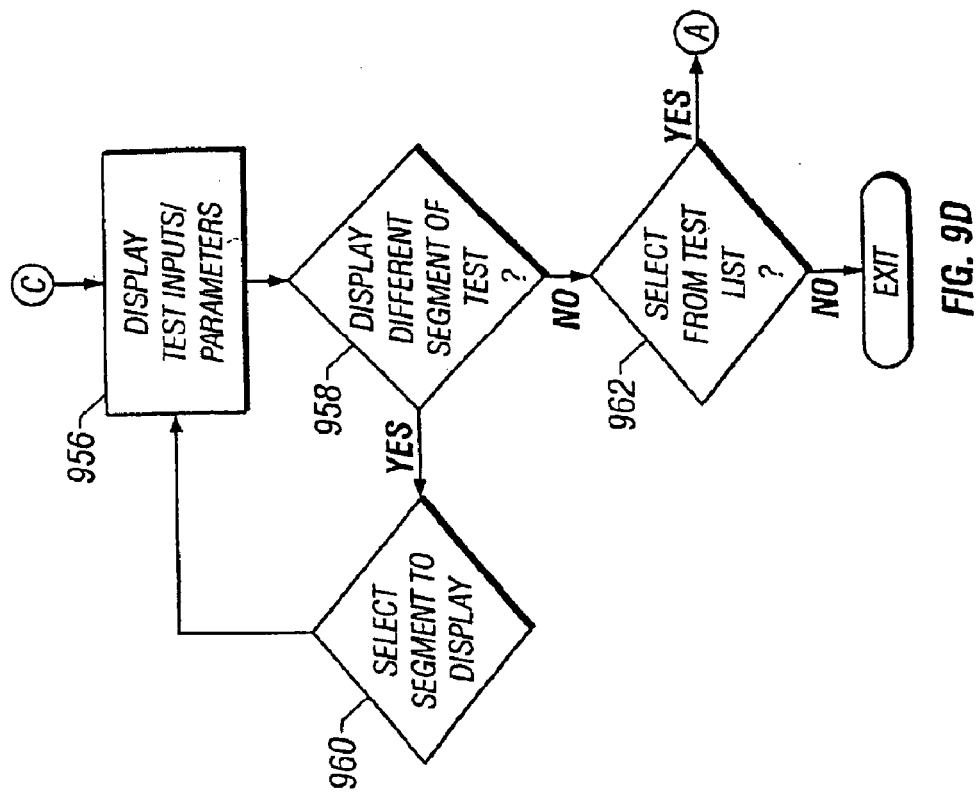

FIG. 9D is a flowchart illustrating the preview screen, which is responsive to the preview button 906 on the main directory display 900 and the test list screen block 926, and allows the operator to preview any test parameters. At block 956, the system displays test inputs and parameters. The system then proceeds to decision block 958 where the operator may choose to select a different segment of the test. If the operator chooses to display a different segment, then the system proceeds to decision block 960 where the operator selects which segment to display, and then returns to block 956. If the operator chooses not to display a different segment of the test, then the system proceeds to decision block 962 where the operator chooses whether to select from the existing test list. If the operator chooses to select from the existing test list, then the system proceeds to FIG. 9B, block 916. If not, then the system returns to the display main directory at block 900.

FIG. 9E represents the selection of the run/stop screen responsive to the run/stop navigational button 912 on the main directory screen 900. This screen allows the operator to run or stop the test. At block 964, the system displays the test time and irradiance parameters. The system then proceeds to decision block 966 where the operator chooses whether to run the test. If yes, then the system proceeds to the main screen to be discussed below with respect to FIG. 9F. If not, then the system proceeds to decision block 968 where the operator decides whether to stop the test. If yes, then the system returns to block 964. If no, then the system proceeds to decision block 970 where the operator decides whether to reset the test. If yes, then the system returns to block 964. If not, then the system returns to the main directory display at block 900.

Figure 9F:
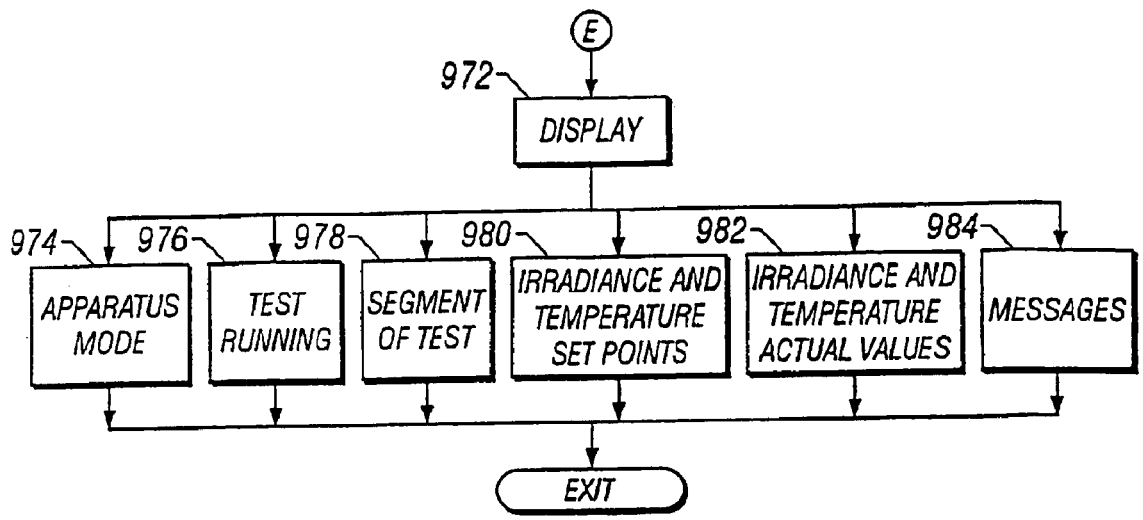

FIG. 9F is a flow chart, illustrating the selection of the main screen button 904 from the main directory display 900. At block 972, the system displays all main test information. Block 974 displays the apparatus mode. Block 976 displays the name of the test that is currently running (ultraviolet, spray condensation cycle, etc.). Block 978 displays the run memory segment of the currently running test. Block 980 displays the set points for the irradiance and temperature of the segment. Block 982 displays the actual values for the irradiance and temperature of the segment currently running. Block 984 displays messages about the condition of the currently running test. When done, the system returns to the main directory display at block 900.

Figures 9G, 9H:
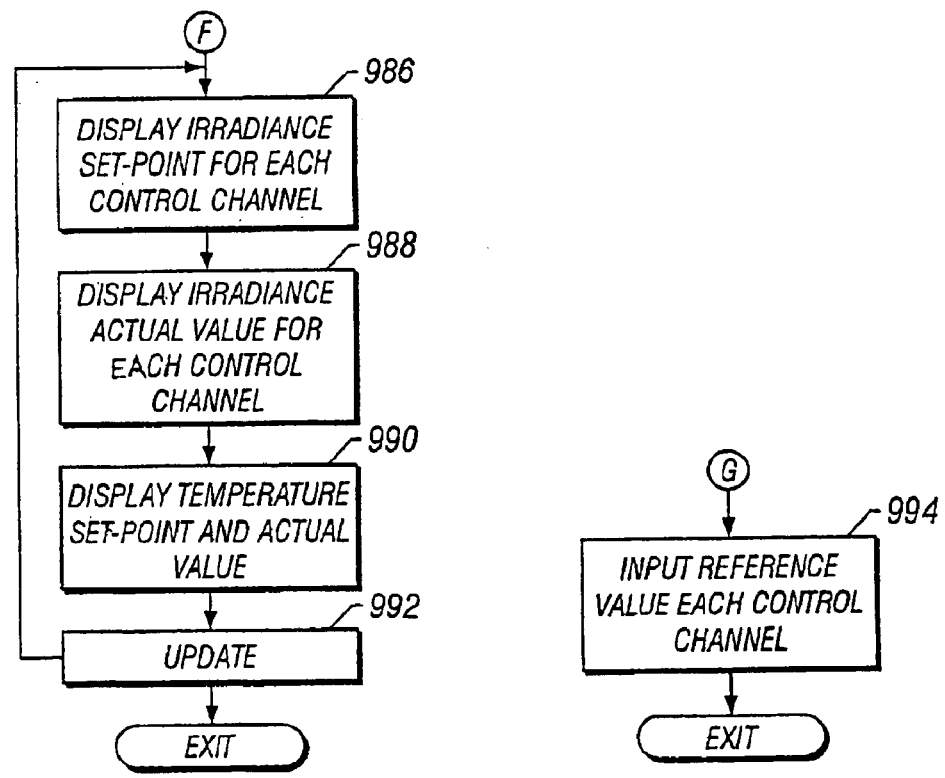

FIG. 9G is a flowchart illustrating the selection of the monitoring screen, which is responsive to the monitor button 908 on the main directory screen 900. At block 986, the system displays the irradiance set point for each control channel. At block 988, the system displays the actual value of the irradiance for each control channel. At block 990, the system displays the temperature set point and actual values for each control channel. At block 992, the system is updated. The system then returns to the main directory display at block 1000.

FIG. 9H is a flowchart illustrating the selection of the irradiance calibration screen, which is responsive to the irradiance calibration button 910 on the main directory display screen 900. This screen allows the operator to enter the calibrator's module reference values written down by the operator during the calibration procedure discussed below with respect to FIG. 10. At block 994, the operator inputs the reference value for each control channel. The system then returns to the main directory display at block 900.

Figure 10:
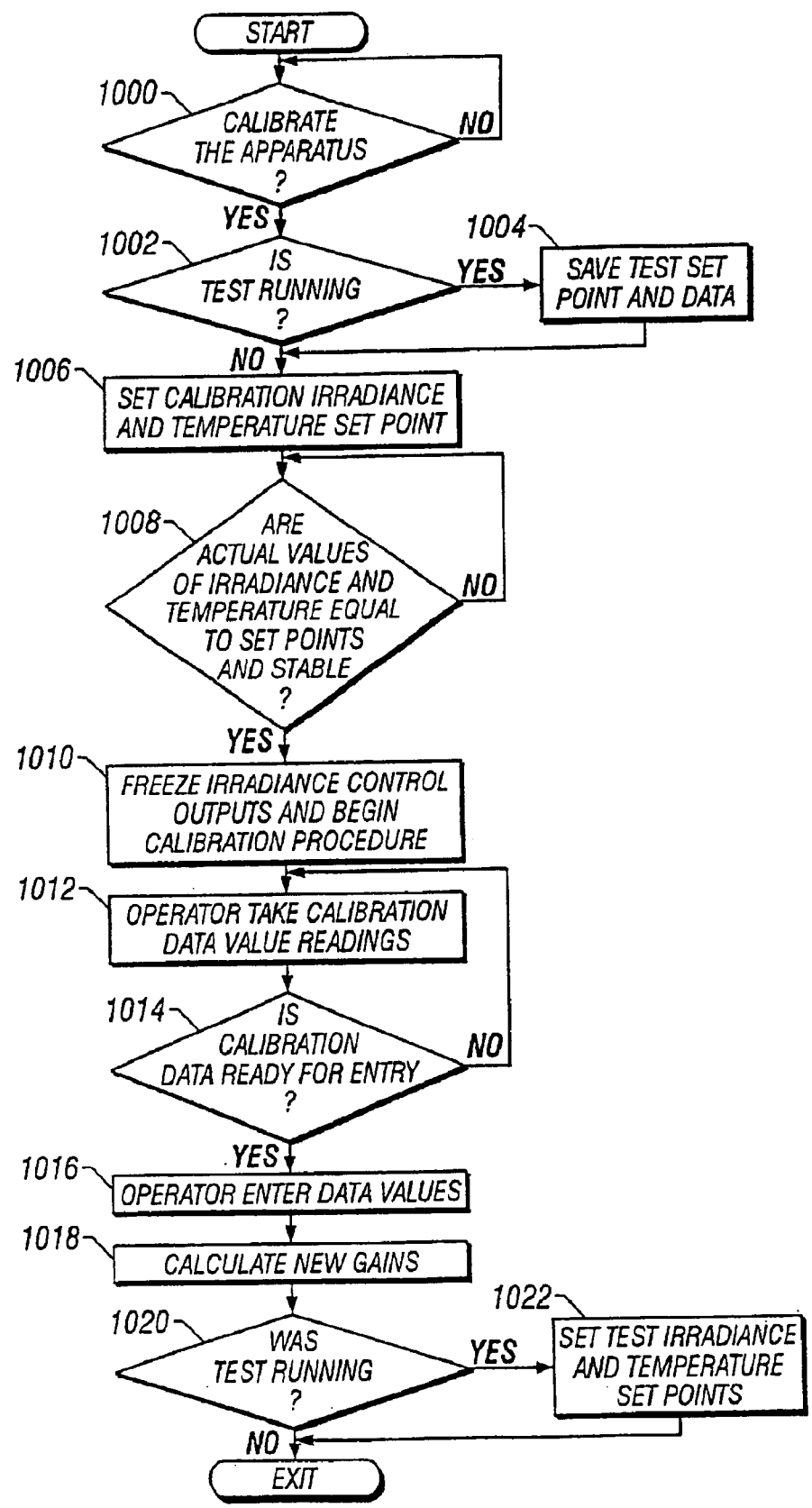
FIG. 10 is a flowchart illustrating the calibration procedure in accordance with the present invention.

FIG. 10 is a flowchart illustrating the calibration procedure for the present invention. During this procedure, the test module which is disposed in the door pocket is removed from the designated first position and the calibration module substituted into the first position. It will be recognized by one of skill in the art that the calibration procedure must be performed every four hundred hours as per industry standard. However, an operator may calibrate the machine at any time during a test, or the controller may be programmed to display a message requesting calibration as desired by the operator, or, when the lamps do not respond as designed to the above monitor controls procedure.

At block 1000, the controller asks if the operator desires to calibrate the apparatus. If no, then the controller enters a loop and inquires again after a predetermined period. If yes, then at block 1002 the controller determines if a test is currently running. If so, then at block 1004 the controller saves to memory the irradiance set point, temperature set point, other test data and the duration of the test before proceeding. At block 1006, the operator must set the calibration irradiance and temperature set points. At decision block 1008 the controller will then determine if the actual measured values of irradiance and temperature are equal to the set points and are stable. If not, then the controller enters a loop for a specified period of time before inquiring again at decision block 1008. If yes, then at block 1010 the controller freezes all four of the control channel outputs to the ballast so that the lamp output will not fluctuate.

The test module in the first position is removed and replaced with the calibration module, as described above, which is automatically acknowledged by the controller that this is the proper sensor in the proper position. The calibration module also automatically identifies the type of ultraviolet lamp (UV-A, UV-B or UV-C) or obtains the information from the controller. If there is a conflict, the calibration module will be determined as correct. The calibration module generates a reference value, which at block 1012 the operator must obtain (i.e., enter manually by hand). The calibration module may then be removed and replaced with the working test module for the first position. Note, this procedure is repeated for each test module position.

After each test module position the controller asks at block 1014 if the calibration data of reference values is ready for entry into the controller. If no, then the operator takes the calibration data reference value for the for the next test module position. If yes, then at block 1016 the operator enters the reference data values into the controller. At block 1018 the controller calculates new gain values for adjusting the ballast control signal. At block 1020 the controller asks whether a test was running. If yes, then at block 1022 the test irradiance and temperature set points are reset and the test resumes. If no, then the controller exits the calibration procedure. Preferably, the controller includes a processing unit and memory that stores programming instructions, that when read by the processing unit, causes the controller to function to operating testing and calibration procedures.

Figure 11:
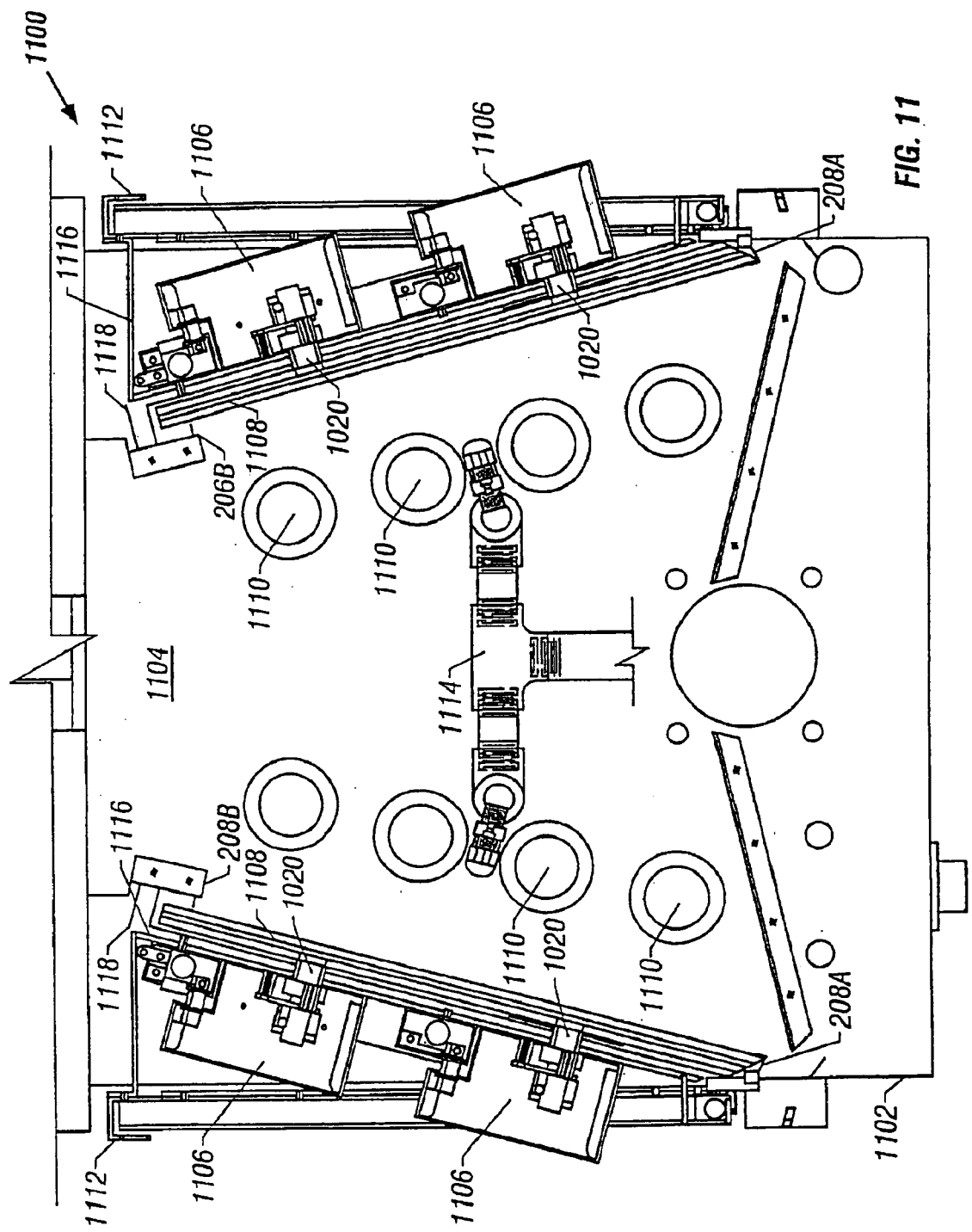
FIG. 11 is a partial cross sectional view of an apparatus embodying the present invention.

FIG. 11 is a partial cross-sectional view of an apparatus embodying the present invention. The apparatus 1100 includes a tank 1102 defining a test chamber 1104, test modules 1106, specimen holders 1108, lamps 1110, a door 1112, and a moisture system 1114. The test chamber 1104 in this embodiment has eight lamps 1110. As discussed above, these lamps may be fluorescent, xenon, or any other suitable ultraviolet light source. The specimen holders 1108 are positioned on the specimen mounting apparatus 208, which includes lower rails 208A and upper rails 208B and is defined in a plane substantially parallel to the plane in which the lamps are defined. The lamps 1110 are positioned at a distance from the specimen holders 1108, consequently providing the desired weathering effects. Further, the moisture system 1114 introduces an additional weathering effect as is conventional in the art.

The door 1112 has a pocket 1116 formed therein for mounting the test modules 1106. This is advantageous in that the temperature sensitive electronics of the test modules have been removed from the test chamber 1104 and positioned outside thereof. As a result, an exceptionally stable signal is generated. Accordingly, control of the irradiance is more stable without the signal drift. As a result, the lamps 1110 last longer, thus reducing costs. A small gap 1118 is shown between the floor of the pocket 1116 and the specimen holders 1108. This is to avoid any unwanted or unintended influence on the testing procedures or results.

FIG. 11 further shows that a portion 1020 of the test module 1106 projects through the floor of the pocket 1116 in order to detect the irradiance of the two lamps 1110 adjacent thereto. The end of the sensor projecting portion has an input for transferring the ultraviolet light via light pipe technology to the test sensor disposed within the test module. An optical filter may be used in connection with the test sensor and may be built into the optical photodiode. The present invention is particularly advantageous because the input is disposed substantially as a specimen in the specimen holder 1108. Accordingly, the sensor reading and associated irradiance signal accurately represent the irradiance witnessed by the specimens. The test modules 1106 are independently removable from the door as discussed above. Further, the calibration module is substituted for the test module into the same position of the test module after removal, for calibration of the weathering apparatus as discussed above.

The invention is not limited to the particular details of the apparatus for methods shown or described and other modifications and applications may be contemplated. Certain other changes may be made in the above-described apparatus without departing from the true spirit and scope of the invention here involved. For example, an embodiment of the present invention may instead, or additionally, include software to perform some or all of the functions. It is intended, therefore, that the subject matter of the above depiction shall be interpreted as is illustrative and not in a limiting sense.

What is claimed is:

1. An accelerated weathering apparatus, comprising:
    an enclosure having at least one door for access to a test chamber defined within the enclosure;
    a specimen mounting apparatus disposed within the test chamber for supporting specimen holders;
    a light source disposed within the test chamber for producing light in the test chamber;
    a power source for powering the light source;
    a test module removably disposed in a pocket defined in the at least one door for detecting irradiance in the test chamber produced by the light source and generating an irradiance signal representative of the detected irradiance;
    a ballast connected to the light source for controlling the amount of power received by the light source from the power source;
    a controller connected to the test module and the ballast which controls operation of the ballast by transmitting a ballast control signal, whereby the controller adjusts the ballast control signal in response to the irradiance signal received from the test module in order to maintain a desired irradiance within the test chamber; and a calibration module for detecting the irradiance in the test chamber in order to generate and display a reference value which represents the detected irradiance, whereby the calibration module interchangeably replaces the test module in the pocket to detect the irradiance in the test chamber and display the reference value on the calibration module which is inputted to the controller for adjusting the ballast control signal.

2. The apparatus as recited In claim 1, wherein the light source includes a plurality of lamps.

3. The apparatus as recited in claim 1, wherein the pocket is formed in the at least one door such that a recess is provided on the exterior surface of the at least one door so that the test module and calibration module may each be interchangeably, removably disposed within the pocket when the at least one door is in a closed position.

4. The apparatus as recited in claim 1, wherein the light source is selected from the group of lamps that generate ultraviolet light in the UV-A, UV-B, and UV-C ranges.

5. The apparatus as recited in claim 1, wherein the calibration module includes at least two internal calibration routines which allow calibration of at least two different types of ultraviolet light while using the same calibration module.

6. The apparatus as recited in claim 1, wherein the test module further includes a plug which interfaces with a receptacle disposed in the pocket in order to connect the controller and the test module such that the controller is automatically connected to the test module when the test module is disposed within the pocket.

7. The apparatus as recited in claim 1, wherein the test module includes at least one test sensor of an optical photodiode type.

8. The apparatus as recited in claim 1, wherein the calibration module includes a reference sensor of an optical photodiode type.

9. The apparatus as recited in claim 1, wherein the test sensor has a liner slope of responsivity in the ultraviolet range.

10. The apparatus as recited in claim 1, wherein the controller includes a processing unit and memory that stores programming instructions, that, when read by the processing unit, causes the controller to function to: receive a set-point input for the desired irradiance signal; and begin a testing procedure including the steps of: outputting a ballast control signal to the ballast based upon the set-point; receiving the irradiance signal input from the test module: adjusting the ballast control signal based upon gain between the set-point and the irradiance signal; outputting an adjusted ballast control signal; and repeating testing procedure steps for a desired period of time.

11. The apparatus as recited in claim 1, further including a temperature sensor connected to the controller for monitoring the temperature within the test chamber, generating a temperature signal, and transmitting the temperature signal to the controller for adjusting the heater control signal in order to maintain the desired temperature within the test chamber.

12. The apparatus as recited in claim 1, further including a temperature sensor connected to the controller for monitoring the temperature within the test chamber, generating a temperature signal, and transmitting the temperature signal to the controller for adjusting the ballast control signal in order to maintain the desired irradiance within the test chamber.

13. The apparatus as recited in claim 1, wherein the test module amplifies and filters the irradiance signal to reduce frequency noise.

14. The apparatus as recited in claim 13, wherein the reduction in frequency noise is achieved by converting a high impedance signal to a low impedance signal with gain.

* * * * *